United States Patent [19]

Ryder

[11] Patent Number: 5,372,129
[45] Date of Patent: Dec. 13, 1994

[54] OXYGEN DILUTION DEVICE FOR MAINTAINING AN ESSENTIALLY CONSTANT PROPORTION OF PRIMARY GAS IN A DILUENT GAS

[76] Inventor: Steven L. Ryder, 1334 W. Woodcrest Ave., Fullerton, Calif. 92633

[21] Appl. No.: 902,702

[22] Filed: Jun. 23, 1992

[51] Int. Cl.[5] .......................... A62B 7/00; A62B 9/00; G05B 1/00; A61M 16/00
[52] U.S. Cl. ....................... 128/205.11; 128/204.25; 128/204.29
[58] Field of Search ................... 128/203.12, 203.25, 128/204.18, 204.24, 204.25, 205.11, 205.24, 204.29; 137/3, 896–898, 605

[56] References Cited

U.S. PATENT DOCUMENTS

| | | | |
|---|---|---|---|
| 3,526,239 | 9/1970 | Oroza | 128/204.29 |
| 3,526,241 | 9/1970 | Veit | 128/204.29 |
| 3,830,257 | 8/1974 | Metivier | 128/205.11 |
| 3,875,957 | 4/1975 | Veit et al. | 128/205.11 |
| 4,036,253 | 7/1977 | Fegan et al. | 128/205.11 |
| 4,495,946 | 1/1985 | Lemer | 128/205.11 |

*Primary Examiner*—Kimberly L. Asher
*Attorney, Agent, or Firm*—John E. Vanderburgh

[57] ABSTRACT

There is disclosed a device adapted to accurately deliver a selected concentration of a primary gas in a diluent gas, such as ambient air. The device of the invention includes a hollow diluter body having generally opposed ports for the ingress of a primary stream of gas and the egress of a dilution stream of gas. The interior of the body defines a dilution chamber and a vent chamber, both of which are open to the egress port. The top wall of the body is provided with a port for communication between the dilution chamber and the exterior of the body. A vent port in the housing provides communication between the vent chamber and the exterior of the device. Pressure sensitive sealing means normally closes the vent chamber to prevent communication between the chamber and the exterior of the device and is operative responsive to pressure in the vent chamber to open and allow communication between the vent chamber and the exterior of the device through the vent port.

4 Claims, 3 Drawing Sheets

% O₂ in diluted stream,
no down stream back pressure

OXYGEN DILUTION DEVICE FOR MAINTAINING AN ESSENTIALLY CONSTANT PROPORTION OF PRIMARY GAS IN A DILUENT GAS

FIELD OF THE INVENTION

This invention relates to a device for the dilution of one gas in another and more particularly, to respiratory inhalation therapy devices in which oxygen is diluted in air.

BACKGROUND OF THE INVENTION

A primary objective in the care of patients having respiratory problems is to reduce the work of breathing and to provide supplemental oxygen to the patient. There are a number of devices, referred to herein as oxygen dilution devices, available for the clinician to provide to the patient oxygen in the range of from about 24% to 100%. The amount of oxygen required depends upon the diagnosis of the patient and blood gas analysis. These devices normally utilize the Bernoulli principal and are designed to provide a precise inspired oxygen concentration from 24% to 60% at high total gas flow. It is important that total gas flow be maintained at a high level in order to meet the respiratory demands of the patient so that the delivered concentration of oxygen is not diluted secondarily by abnormally high minute ventilation.

Most of the oxygen dilution devices presently available provide means for adjusting the concentration of oxygen in the air stream exiting the device. These devices generally comprise a body in which the primary oxygen stream is received and which is provided with one or more ports which open to the exterior of the body for the intake of ambient air. The flow of the primary oxygen stream through the dilution body decreases the pressure within the body causing ambient air to be drawn into the body to mix with the oxygen stream and passed on to the patient. By varying the size of the air intake port to increase or reduce the flow of air into the diluter, the concentration of oxygen in the air stream can be varied. Conventionally, the dilution devices include a plurality of ports to the exterior which vary in size and which are provided with a covering device so that a port of desired size is opened to the exterior while the other ports are closed. Examples of various designs of oxygen dilution devices are shown in U.S. Pat. No. 3,794,072, issued Feb. 26, 1974 to Diedrich et al; U.S. Pat. No. 3,850,171, issued Nov. 26, 1974 to Ball et al; U.S. Pat. No. 3,913,607, issued Oct. 21, 1975 to John Price; U.S. Pat. No. 3,977,432, issued Aug. 31, 1976 to Vidal; and U.S. Pat. No. 4,848,333, issued Jul. 18, 1989, to Richard B. Waite. As illustrated in these patents, the oxygen dilution device is incorporated in the air hose leading to a mask. The primary oxygen stream is introduced into the hose and air is drawn in due to the reduced pressure of the oxygen flowing through the dilution device to dilute the primary oxygen stream prior to reaching the patient.

A primary problem with these devices occurs when there is an obstruction in the passage leading which produces a restriction of the total gas and a back pressure in the diluter body. In this case, the flow of the primary stream, which is under pressure, remains essentially constant while the pressure in the diluter increases due to the back pressure thus reducing air intake. This results in an enrichment of oxygen in the diluted stream reaching the patient which may lead to injury to an oxygen sensitive patient, such as one suffering with emphysema, and at the least results in a loss of control over the concentration of oxygen delivered to the patient. Such downstream resistance may be caused by a small amount of phlegm or condensation in the line which is sufficient to produce a back pressure and resultant increase in oxygen concentration to the patient. In addition, most dilution devices used in respiratory care are attached to a face mask in which large openings are provided for the egress of the high flow air stream which is not inhaled and to prevent the build-up of $CO_2$. Although practitioners often assume that the concentration settings of the dilution device accurately indicate the true concentration of oxygen delivered to the patient, this is not a valid assumption because of back pressure created at the face mask by the high total gas flow. As a result, the respiratory clinician and/or attending nurses must be constantly on alert to such a situation and the inhalation system as well as the blood gases must be monitored if dilution devices are to be used with any degree of confidence.

SUMMARY OF THE INVENTION

Consequently, it is an object of the present invention to provide a gas dilution device which can provide a precise concentration of oxygen in the patient air stream thereby to substantially reduce the danger of undesirable variations in the oxygen concentration in the patient air stream.

Another object of the present invention is to provide an improved oxygen dilution device for respiratory care which includes valve means for maintaining reduced pressure within the device even in the event of downstream back pressure.

Another object of the invention is to provide a convenient means for adjusting oxygen concentration in the patient air stream without the undue multiplication of component parts and jets as is conventional with devices currently available in the art.

Yet another object of the invention is to provide an dilution device which includes a secure locking mechanism for securing the oxygen concentration selector to prevent the inadvertent movement of the selector.

It will be understood that while the invention will be described herein in connection with devices for diluting oxygen in an air stream, the invention may be applied to the dilution of other gases in air or dilution streams of gases other than air.

As used herein the term "primary gas" refers to the gas to be diluted which is caused to flow through the dilution device at sufficient velocity to create a reduced pressure within the device according to the venturi principal. The term "diluent gas" refers to the ambient gas drawn into the device and mixed with the primary gas stream. The term "dilution stream" refers to the mixed stream of primary gas and diluent gas.

The foregoing objects and other advantages of the present invention are achieved by a device adapted to dilute the concentration of a primary gas with a diluent gas, such as ambient air. The device of the invention includes a hollow diluter body having generally opposed ports for the ingress of a primary stream of gas and the egress of a dilution stream of gas. The interior of the body defines a dilution chamber and a vent chamber, both of which are open to the egress port. The top wall of the body is provided with a port for communication between the dilution chamber and the exterior of the body. A vent port in the housing provides communication between the vent chamber and the exterior of the device. Pressure sensitive sealing means normally closes the vent chamber to prevent communication between the chamber and the exterior of the device and is operative responsive to pressure in the vent chamber to open and allow communication between the vent chamber and the exterior of the device through the vent port.

In a preferred embodiment, the bottom wall of the body includes a two position nozzle member which extends into the dilution chamber in line with the ingress port of the primary stream. The valve is provided with two bores, one bore being of larger diameter than the other, and is movable between the large bore and the smaller bore position to vary the stream of primary gas depending upon the desired concentration range of the primary gas in the diluted stream. Means are provided on the top wall for selectively closing the port thereby to vary the size and consequently restrict the amount of ambient air drawn into the dilution chamber for selection of a desired concentration of primary gas within the concentration range.

The invention will be more readily understood from the following detailed description taken in conjunction with the drawings.

DETAILED DESCRIPTION OF THE INVENTION

Figure 1:
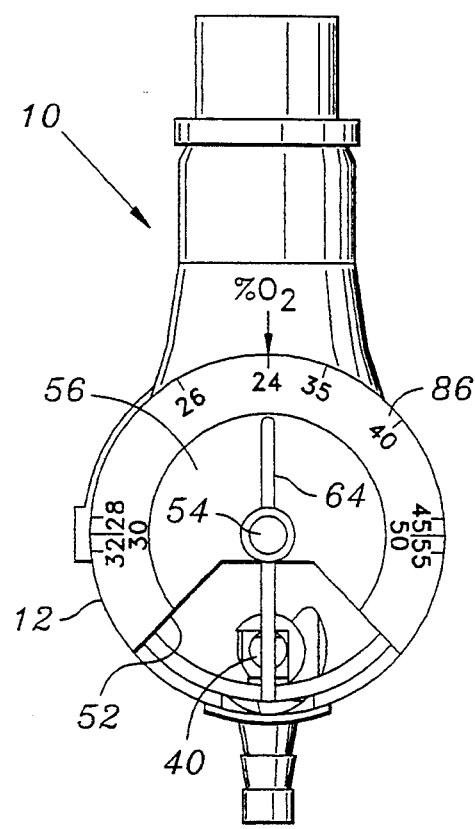
FIG. 1 is a top plan view of the dilution device of the present invention.
Figure 2:
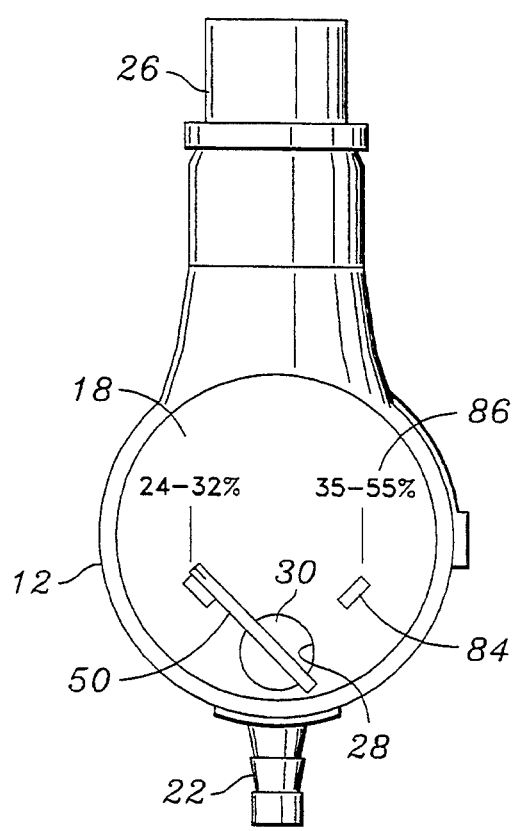
FIG. 2 is a bottom plan view of the device of FIG. 1.
Figure 3:
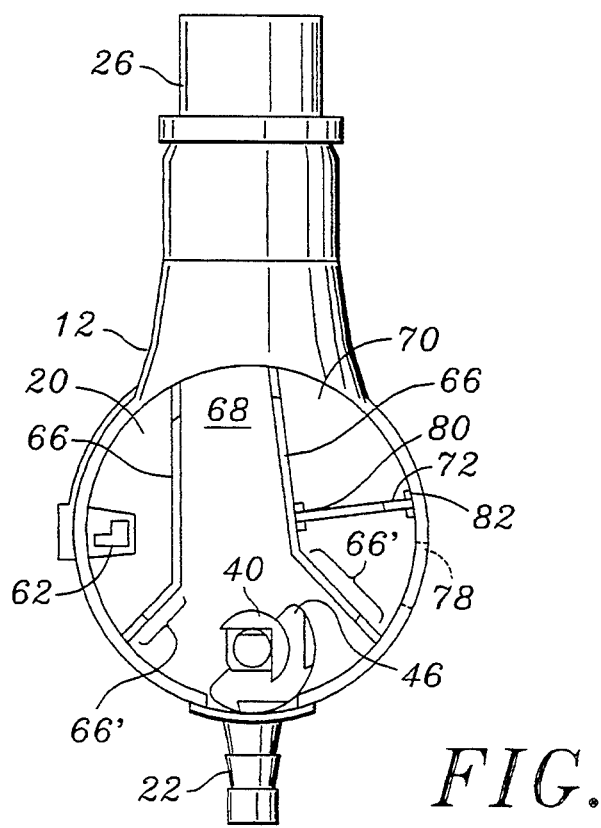
FIG. 3 is a top plan view of the device of FIG. 1 with the top wall removed.
Figure 4:
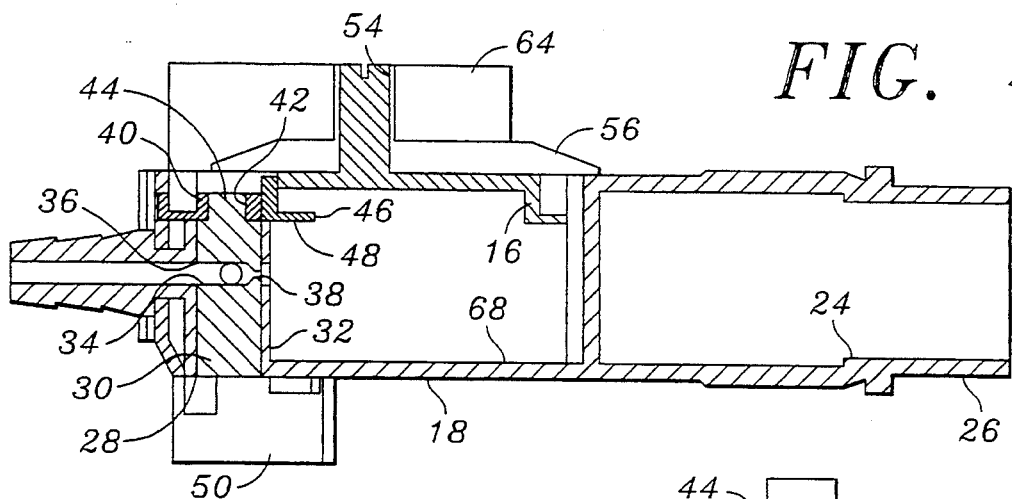
FIG. 4 is a side sectional elevation of the device of FIG. 1 viewed along 4-4.
Figure 5:
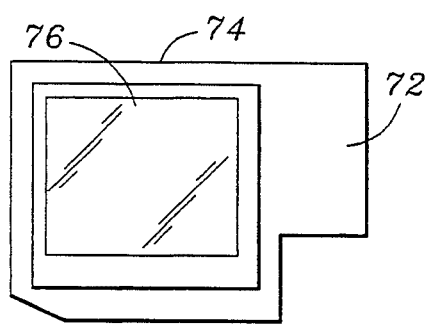
FIG. 5 is front view of the closure wall of the second chamber with the back pressure sensitive closure exploded out and shown in enlarged scale.
Figure 6:
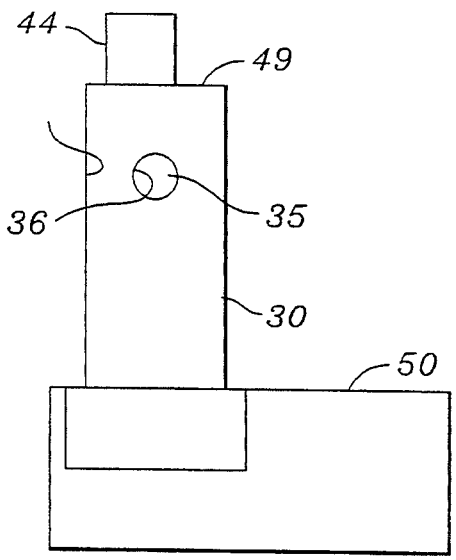
FIG. 6 is a exploded side view partially in section of the device of FIG. 1.
Figure 7:
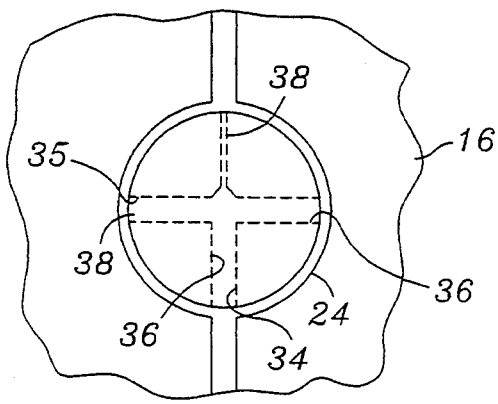
FIG. 7 is a bottom view in enlarged scale and broken away for compactness of illustration of the proportioning valve of FIG. 6 illustrating the valve in the reduced flow position in the device of FIG. 1.
Figure 9:
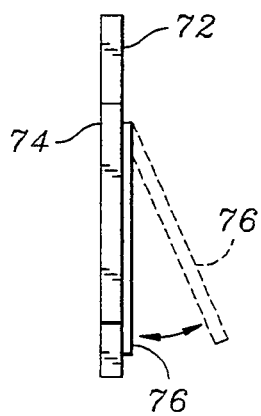
FIG. 9 is a side view of the back pressure sensitive closure shown in FIG. 5.

Referring to the Figures, the dilution device 10 includes a housing 12 having side walls 14, a bottom wall 16 and a top wall 18 defining an interior 20. A generally tubular connector 22 is disposed in the side wall 16 of the housing 12 and the bore of the connector 22 opens into the interior 20 of the housing 12. The connector 22 is designed to be connected to suitable tubing (not shown) for communication with a source of primary gas such as for example oxygen. The opposite end of the housing 12 is provided with an opening 24 leading into a cylindrical member 26 adapted for connection to a mask hose or the like for egress of the dilution stream of the primary gas and air.

The bottom wall 16 of the housing 12 is provided with an opening 28 and a tubular seal 32 extends into the housing 12 immediately adjacent the bore opening of the connector 22. An opposed pair of openings, 33a and 33b, in the wall of the tubular seal 32 are aligned with the bore opening of the connector 22. A cylindrical nozzle member 30 having a diameter essentially the same as the inside diameter of the tubular seal 32 is received in the tubular seal 32 for rotation about its longitudinal axis within the seal. Open ended, perpendicularly intersecting bores 34 and 35 extend through the member 30 normal to its longitudinal axis. One open end 36 of each of the bores 34 and 35 is aligned with the passage opening of the connector 22 depending upon the axial orientation of the nozzle member and the opposite open end 38 is constricted to define a nozzle orifice through which the primary gas enters the housing 12. The nozzle orifice of the bore 34 is smaller than the nozzle orifice of the intersecting bore 35. Rotation of the nozzle member 30 to align bore 34 with the opening of the connector 22 decreases the flow of primary gas as compared to the flow of primary gas when bore 35 is aligned with the connector opening. The nozzle member 30 is secured in the tubular seal 32 by a retainer 40 having a central opening 42 which receives a mounting lug 44 formed on the upper end of the nozzle member 30. The lower end of the retainer 40 is radially extended to define a wing 46, the lower surface 48 of which rides on the upper end of the tubular seal 32 to retain the nozzle member 30 in the seal. A handle 50 is attached to the lower end of the nozzle member 30 to facilitate rotation of the nozzle member.

The upper wall 16 of the housing 12 is cut away to define an air inlet port 52 which communicates with the exterior of the housing. A selector disk 56 overlies the upper wall 16 and is rotatably mounted thereover by an upstanding spindle 54 on the upper wall which extends through a central opening 58 in the selector disk. A portion of the selector disk is cut away to define a segment which corresponds in configuration to the inlet port 52 in the upper wall 16. The lower peripheral edge of the selector disk 56 is provided with a series of indentations or detents 60 which are spaced about the periphery of the disk and cooperate with a spring loaded follower 62 to provide positive stopping action at each of the detent positions. The detents 60 are located to correspond to disc positions overlying the inlet port 52 to partially cover the port restricting the amount of air flow to provide a specific concentration diluent gas in the dilution air stream. A handle 64 is provided on the upper surface of the selective disc for manually rotating the disc.

Disposed in the interior 20 of the housing 12 are a pair of partitions 66 which abut at their upper edges with the top wall 16 and at one end with the housing sidewall 16 adjacent the opening of connector 22. The opposite end of each partition 66 terminates adjacent the egress opening 24 and is free standing. The partitions 66 define a central dilution chamber 68 in which air drawn through the air inlet port is mixed with the primary gas to form the dilution stream. Preferably, as shown, the abutting end portions 66' of the partitions 66 are disposed at an angle to the main body of the partition to correspond to the shape of the inlet port 52 to conform that portion of the dilution chamber 68 underlying the inlet port conform to the configuration of the air inlet port.

A vent chamber 70 is defined between one of the partitions 66, a portion of the housing sidewall 14, and a divider 72. The vent chamber 70 communicates with the exterior of the housing through a vent 78. The divider 72 consists of a frame 74 open at its center carrying a membrane flap 76 affixed to the frame along its top edge by suitable adhesive bonding or sonic welding or the like. The flap 76 normally closes the open area of the frame 74 and seals the vent chamber 70 from the vent 78. In the event of an increase of pressure in the vent chamber 70, the flap 76 is forced away from the frame 76 allowing fluid communication from the vent chamber to the outside through the vent 78. The choice of membrane material for the flap 76 is not critical and good results have been achieved with thin film polyethylene or mylar film. The flap 76 is slightly larger than the opening in the frame so that under normal operating conditions with a reduced pressure within the housing 12 the flap lies tightly against the frame member so that air cannot be entrained through the vent 78. The divider 72 is held in position by opposed channels 80 which are defined between spaced apart ribs 82 carried on the partition 66 and the sidewall 16 of the housing 12.

The bottom wall 16 of the housing 12 is provided with a pair of stops 84 which are positioned to contact the handle 50 of the cylindrical member and to stop its rotation at a point where one of the intersecting bores 34 or 35 is aligned with the inlet opening of the connector 22 and the outlet of the tubular seal 32. Indicia 86 are scribed on the bottom wall 18 for indicating the primary gas dilution ranges as selected by the position of the nozzle member 30. The selector disk 56 is similarly provided with indicia 86 located about its periphery to indicate the concentration of primary gas in the dilution stream as a result of the degree to which the air inlet port 52 is covered by the selector disk. The indicia 86 on the selector disk 56 correspond with the detent positions on the underside of the selector disc.

The housing 12, including the tubular seal 32, is preferably molded as a single piece from a suitable molded plastic material such as for example polyethylene or ABS polymer and co-polymer. The partitions 66, which can be made from the same material, are affixed in their respective positions to form the dilution chamber 68 and the vent chamber 70 and the divider 72 inserted in the channels 80 to close the vent chamber. The nozzle member 30 is inserted into the tubular seal 32 through the opening in the bottom wall 16 and the retainer 40 is affixed on the mounting lug 44 on the upper end of the nozzle member 30 to retain it in the bore of the tubular seal 32. The connector 22 is affixed in the housing 12 and the housing assembly is completed by affixing the upper wall 16 by suitable adhesive or by sonic welding over the top edge of the sidewalls 14 of the housing 12 with the cutout segment aligned with the diverging portion of the partitions 66 to define the air inlet port 52. The selector disk 56 is located over the upper wall 16 with the spindle member 54 extending through the central opening in the disk. The selector disk 56 is held on the spindle member 54 by a retainer clip snapped in a groove formed in the spindle member as is conventional in the art. During assembly the selector disk 56 is also aligned so that the edges of the segment are aligned with the edges of the segment of the cover disc and the upper edges of the partitions 66.

In operation a tube (not shown) leading to a source of primary gas, i.e., oxygen, is inserted over the connector 22 for leading the primary gas through the nozzle member 30 into the dilution chamber 68. The nozzle member 30 is rotated in the tubular seal 32 to a selected position where one of the two intersecting bores, 34 or 35, is aligned with the openings 33a and 33b in the tubular seal 32 for the ingress of the primary gas into the dilution chamber 68. The choice of which of the bores to* be used depends upon the desired concentration range of the primary gas in the dilution stream. Thus bore 34, with its smaller nozzle, is selected when the desired concentration is to be in the range of about 24% to about 32% and bore 35, because of its larger nozzle, being selected when the desired concentration range is about 35% to about 55%. As explained, the nozzle member handle 50 is rotated clockwise or counter clockwise until it engages one of the two stop members on the bottom wall 18 of the housing 12, depending upon the desired dilution range for the primary gas.

The retainer 40 and the wing 46 formed thereon rotate with the nozzle member 30 and the stops on the wing prevent contact the lug on the disk handle 64 to prevent rotation of the selector disc in one or the other direction depending upon the position of the nozzle member and the retainer. The flow of the primary gas through the nozzle of the selected bore reduces the pressure in the dilution chamber 68 and outside air is drawn into the dilution chamber through the air inlet port 52 where it mixes with the primary gas to form the dilution stream. The dilution stream exits the housing 12 through the egress opening 24 and flows to the use point, i.e. a patient.

The selector disc 56 is rotated in its permissible direction to one of the dilution points which is positively indicated by the urging of the lock follower 62 into the detent 60 corresponding to the selected dilution as indicated by the indicia 86 on the selector disk. Rotation of the selector disc 56 brings the leading edge of the cutout segment in the disk out of alignment with the corresponding edge of the air inlet port 52 thus partially closing the air inlet port and restricting the flow of air into the dilution chamber 68. The more that the selector disc 56 is rotated the more restricted the air inlet port 52 becomes and the greater the concentration of primary gas in the dilution stream. The dilution stream exits the dilution chamber body at the outlet side which is connected to a hose leading to the using location.

Any obstruction in the line leading to the use point will produce resistance to the flow of the dilution stream which results in back pressure in the dilution chamber 68 and in the vent chamber 70 which is also open to the egress opening 24. The back pressure acts against the membrane flap in the divider 72 causing it to open providing fluid communication between the vent chamber 70 and the exterior of the device 10 through the vent 78 and pressure in the interior of the housing 12 is relieved and normal operating pressure is restored in the dilution chamber. Once the backpressure is relieved, the membrane flap of the divider 72 closes and the vent chamber is resealed. In this manner the back pressure does not restrict the intake of dilution air which can result in unduly high concentration of primary gas in the dilution stream.

The following is an example of the device as described above utilized to dilute a primary stream of oxygen in air. The device was operated with no down stream resistance at oxygen settings ranging from 24% to 60%. The percent oxygen in the dilution stream was analyzed at each of the settings by a probe in the gas stream at the output end of the device. The probe was connected to a fuel cell and signal from the cell was digitized and read out by a digital monitor. Following this the device was again operated at the same range of oxygen settings but this time a down stream resistance was simulated by reducing the outflow orifice at the output end of the apparatus from its normal diameter of 16.25 mm to 6 mm in diameter. The oxygen content of the dilution steam was again analyzed as described above. The flow rate of oxygen was 3 liters per minute. The difference in oxygen concentration of the dilution steam with no resistance and that with resistance it was reported as $O_2\%$ difference. The results are reported in Table 1 below.

TABLE 1

DEVICE WITH BACK PRESSURE COMPENSATION ACCORDING TO THE EFFECT OF BACK PRESSURE

| INVENTION $O_2\%$ SETTING | $_2\%$ ANALYZED | FLOW RATE LPM | % INCREASE $O_2$ W/RESISTANCE | $O_2\%$ DIFFERENCE |
|---|---|---|---|---|
| 24 | 24 | 3 | 30 | 6 |
| 26 | 26 | 3 | 30 | 4 |
| 28 | 28 | 6 | 32 | 4 |
| 30 | 30 | 6 | 34 | 4 |
| 32 | 32 | 6 | 35 | 3 |
| 35 | 35 | 9 | 44 | 9 |
| 40 | 40 | 12 | 48 | 8 |
| 45 | 45 | 12 | 52 | 7 |
| 50 | 50 | 15 | 57 | 7 |
| 55 | 56 | 15 | 64 | 9 |
| 60 | 60 | 15 | 69 | 9 |

The same test protocol was applied to an oxygen device constructed in accordance with in U.S. Pat. No. 3,794,072. Price, et al. The results are reported in Table 2.

TABLE 2

PRIOR ART DEVICE/ EFFECT OF BACK PRESSURE

| $O_2\%$ SETTING | $O_2\%$ ANALYZED | FLOW RATE LPM | % INCREASE $O_2$ W/RESISTANCE | $O_2\%$ DIFFERENCE |
|---|---|---|---|---|
| 24 | 24 | 3 | 44 | 20 |
| 26 | 26 | 3 | 44 | 18 |
| 28 | 29 | 6 | 45 | 17 |
| 30 | 31 | 6 | 46 | 16 |
| 35 | 34 | 9 | 90 | 55 |
| 40 | 39 | 12 | 93 | 53 |
| 50 | 53 | 15 | 95 | 45 |

Figure 8:
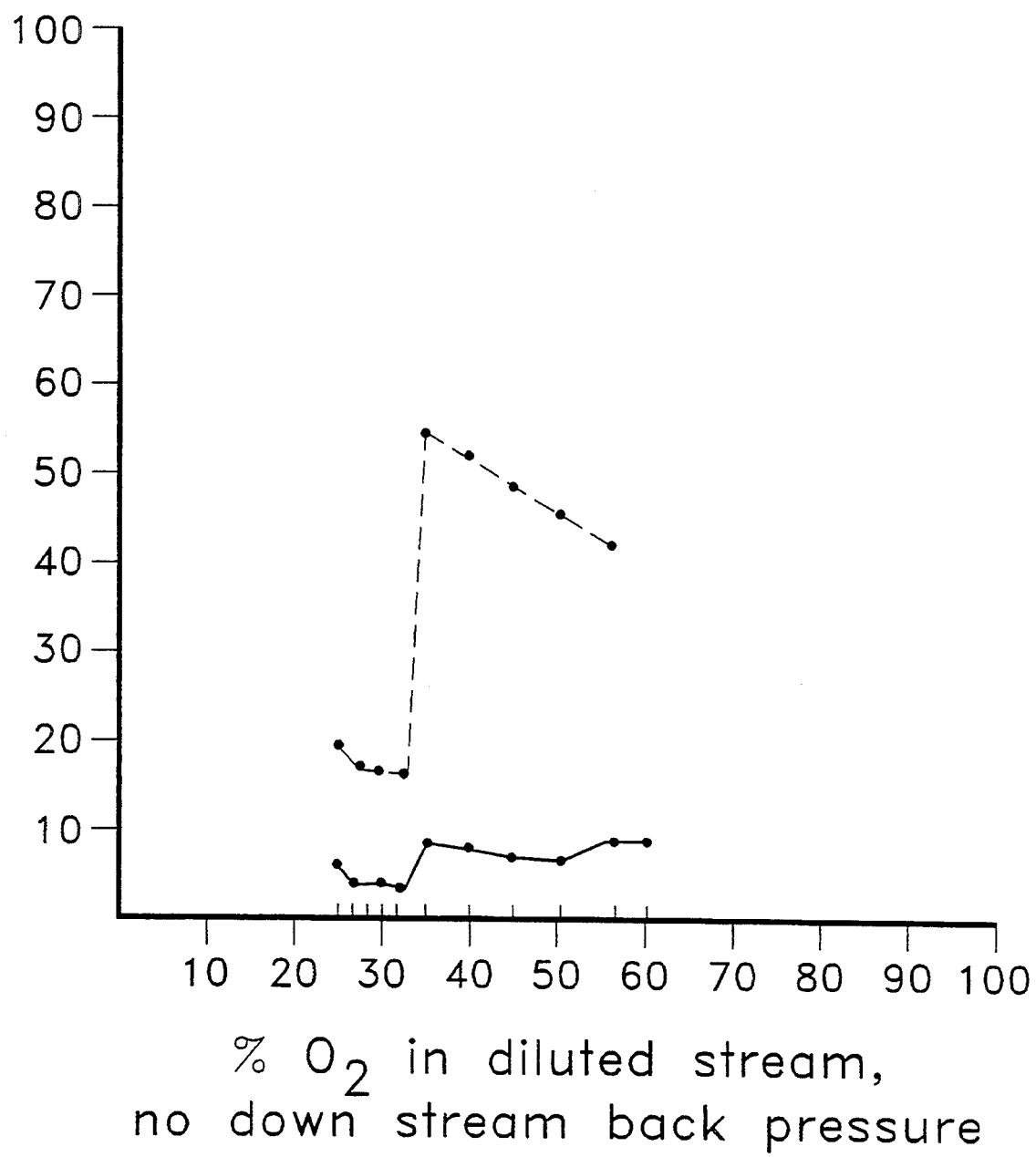
FIG. 8 is a plot of the percent increase in oxygen in the dilute stream with no downstream back pressure against the percent increase in oxygen in the diluted stream with downstream back pressure.

FIG. 8 is a plot of the oxygen concentration in the diluted steam with no back pressure versus $O_2\%$ difference in the oxygen concentration of the dilution stream as a result of the back pressure. The dashed line represents results obtained using the prior art device and the solid line represents the results using the device of the present invention.

It will be understood that the divider 72 in the vent chamber 70 which constitutes the valve for equalizing back pressure within the device maybe otherwise constructed. For example, the valve maybe located in pressure chamber in the sidewall of the device 10 rather than as a divider 72 as described. However, for economy of manufacture and assembly, it is preferred to use the divider 72 and flap arrangement as illustrated.

In addition to substantially reducing the effect of back pressure on the concentration of the primary gas in the dilution stream it will be appreciated that the diluter of the present invention is convenient to use. All that is required is to dial the concentration range to set the proper bore for the cylindrical member and then to dial the specific concentration within the selected concentration range. There is no necessity for assembly or disassembly to change parts as is required in many of the commercially available designs.

When utilized for respiratory care or as part of the oxygen delivery system for a patient. The device of the present invention substantially reduces the effect of down steam obstacles which may cause sufficient back pressure to increase the concentration of oxygen in the dilution gas. The device of the present invention substantially reduces the necessity for monitoring the oxygen content of the output of the device.

As will be understood by those skilled in the art, various arrangements other than those described in detail in the specification will occur to such persons skilled in the art, which arrangements lie within the spirit and scope of the invention. It is, therefore, to be understood that the invention is to be limited only by the claims appended hereto.

Having described the invention, I claim:
What is claimed is:

1. A gas dilution device having means for continuously supplying an essentially constant proportion of a primary gas in a diluent gas, said device comprising:
   a. a housing having a top, bottom and side walls defining an interior,
   b. inlet means for connection to a source of a primary gas to be diluted and outlet means for leading said diluted primary gas out of said housing,
   c. a diluent gas inlet port in said housing for direct communication between said first chamber and the exterior of said housing,
   d. partitioning means for dividing the interior of said housing into at least a first and second chamber, said first chamber communicating directly with said inlet means and said outlet means, said second chamber communicating directly with said first chamber, said partitioning means consisting of a pair of wall members extending between said bottom wall and said top wall and abutting at one end with said housing sidewall at a point adjacent said inlet means for said primary gas, said wall members being spaced apart to define therebetween said first chamber and one of said wall members being spaced from said housing sidewall to define said second chamber, each said wall member having a free end opposite said end abutting said housing sidewall, said free ends terminating adjacent said outlet means and being spaced therefrom for communication between said first chamber, said second chamber, and said outlet means, portions of said wall members underlying said diluent gas inlet port being configured to abut said top wall of said housing along the edge of said diluent gas inlet port thereby to provide communication through said diluent gas inlet port to said first chamber only e. closure means on said housing for selectively restricting the flow of diluent gas through said inlet port to said first chamber.

f. a vent port opening between said second chamber and the exterior of said housing, and g. means for sealing said second chamber from said vent port, said means opening to provide communication between said second chamber and the exterior of said housing through said vent port responsive to a build up of back pressure in said interior of said housing to relieve the back pressure thereby to return the inflow of dilution gas to normal and maintaining an essentially constant proportion of primary gas in said diluent gas.

2. The gas dilution device of claim 1 including a two-position nozzle member rotatably mounted in said housing interior, said nozzle member having first and second open-ended through-running bores, one end of said first bore being aligned with said inlet means, the opposite open end of said first bore defining a nozzle orifice means for discharging gas into said first chamber when said nozzle member is in one position and one open end of said second bore being aligned with said inlet means for primary gas and the opposite end of said second bore defining a nozzle orifice means for discharging gas into said first chamber when said nozzle member is in the other position.

3. The dilution device of claim 2 further including a tubular seal in said housing, said tubular seal including a pair of openings aligned with said inlet means for primary gas, said nozzle member being rotatably mounted in said tubular seal for rotation between said first position with said first bore aligned with said openings and a second position with said second bore aligned with said openings in said seal member.

4. The dilution device of claim 2 wherein said nozzle orifice means of said first and second bores are of different diameters.

* * * * *